United States Patent [19]

Wade et al.

[11] Patent Number: 4,946,960
[45] Date of Patent: Aug. 7, 1990

[54] PERESTER COMPOUNDS

[75] Inventors: John R. Wade, Otley; Rodney M. Potts, Leeds; Michael J. Pratt, Menston, all of United Kingdom

[73] Assignee: Vickers PLC, London, United Kingdom

[21] Appl. No.: 107,889

[22] Filed: Oct. 9, 1987

Related U.S. Application Data

[63] Continuation of Ser. No. 902,046, Aug. 26, 1986, abandoned, which is a continuation of Ser. No. 607,774, May 7, 1984, abandoned.

[30] Foreign Application Priority Data

May 9, 1983 [GB] United Kingdom ............... 8312721

[51] Int. Cl.$^5$ ................. C07D 277/60; C07D 277/84; C07D 417/00
[52] U.S. Cl. .................................................. 548/150
[58] Field of Search .......................................... 548/150

[56] References Cited

U.S. PATENT DOCUMENTS

| | | | |
|---|---|---|---|
| 4,026,884 | 5/1977 | Mee | 548/150 |
| 4,129,586 | 12/1978 | Sheppard et al. | 560/32 |
| 4,275,142 | 6/1981 | Hosaka et al. | 430/271 |
| 4,416,826 | 11/1983 | Neckers | 544/106 |
| 4,604,295 | 8/1986 | Humphreys | 427/54.1 |

FOREIGN PATENT DOCUMENTS

| | | | |
|---|---|---|---|
| 125140 | 11/1984 | European Pat. Off. | |
| 125875 | 11/1984 | European Pat. Off. | 260/453 RZ |
| 2804148 | 8/1978 | Fed. Rep. of Germany | 548/150 |
| 1062190 | 12/1983 | U.S.S.R. | |
| 466097 | 5/1937 | United Kingdom | 548/150 |
| 533425 | 2/1941 | United Kingdom | 548/150 |

OTHER PUBLICATIONS

Chemical Abstracts, vol. 102, 70278y.
Chemical Abstracts, vol. 102, 140898y.
Neckers et al., Journal of Polymer Science; Polymer Chemistry, pp. 147–157 (1982).
Neckers et al., Journal Organic chemistry, vol. 44, No. 23, (1979).

*Primary Examiner*—John Kight, III
*Assistant Examiner*—Kriellion Morgan
*Attorney, Agent, or Firm*—Kenyon & Kenyon

[57] ABSTRACT

Perester compounds suitable for causing the polymerisation of addition polymerisable compounds on exposure to radiation have the general formulae

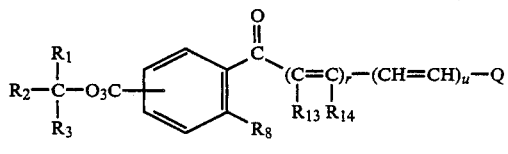

or

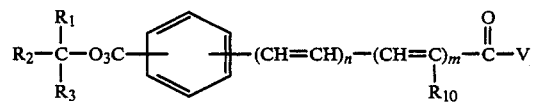

1 Claim, No Drawings

PERESTER COMPOUNDS

This application is a continuation, of application Ser. No. 902,046, filed Aug. 26, 1986, now abandoned, which is a continuation of application Ser. No. 607,774, filed May 7, 1984 now abandoned.

This invention relates to perester compounds and is concerned with such compounds which are suitable for causing the polymerisation of addition polymerisable compounds on exposure to radiation.

According to the present invention there is provided a perester compound having (a) the general formula I

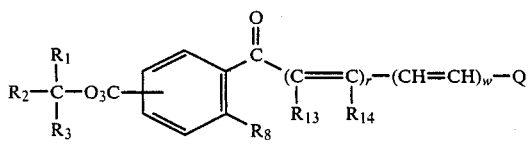

wherein
$R_1$, $R_2$ and $R_3$, which may be the same or different, represent H, alkyl or aryl;
r and w, which may be the same or different, equal 0 or 1;
Q, in the case where r and w both equal zero, represents (1b)

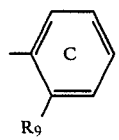

wherein
$R_8$ and $R_9$, when taken together, represent —O—, —S—,

—CH— or a single bond;
Q, in the case where r=1, $R_{14}$ represents H, and $R_8$ and $R_{13}$ together represent the ring members optionally substituted cycloalkan (di) one nucleus which may optionally include a hetero atom and may optionally be fused to an aromatic nucleus, represents (2b) an aromatic or heterocyclic radical, and
Q, in the case where w=0, r=1, $R_8$ represents H, and $R_{13}$ represents H, acyl, heterocyclyl carbonyl, aroyl or

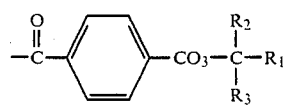

represents (3b)

wherein $R_{12}$ represents alkyl and $R_{15}$ and $R_{14}$, taken together, represent the ring members required to complete a 5- or 6- membered nitrogen containing ring which may be optionally fused to an aromatic nucleus
or (b) the general formula II

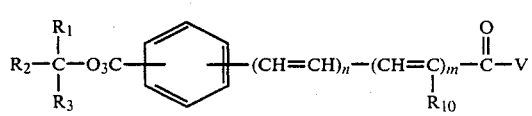

wherein
$R_1$, $R_2$ and $R_3$ have the above meanings;
m and n, which may be the same or different, equal 0 or 1;
$R_{10}$ represents H or alkyl; and
V represents either
(1)

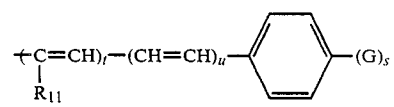

wherein
$R_{11}$ represents H, alkyl, or together with $R_{10}$ the ring members necessary to complete an cycloalkan(di-)one nucleus which may optionally include a hetero atom and may optionally be fused to an aromatic nucleus;
t, u and s, which may be the same or different equal 0 or 1 provided that m,n s,t and u are not all equal to O; and
G represents

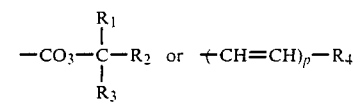

wherein
p equals 0, 1 or 2; and
$R_4$ represents
(1a) an aryl radical,
(2a) an hetero radical,
(3a)

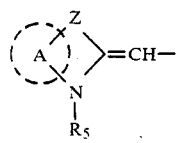

wherein
A represents an aromatic nucleus;
Z represents O,S or Se; and
$R_5$ represents H, alkyl or phenyl;
(4a) provided that m, n, t, u and p are all O,

wherein $R_6$ and $R_7$, which may be the same or different, represent H, alkyl, aryl, or an alkyl chain $-(CH_2)_x-$ where x is 2,3 or 4 covalently bonded to the adjacent ring, or (5a) provided that m, n, t u and p are not all zero, H, alkyl, alkoxy, phenoxy, a polymeric backbone, or N $R_6$ $R_7$ wherein $R_6$ and $R_7$ have the above meanings;

or (2)

taken together with $R_{10}$, the ring members optionally cycloalkan(di)one ring nucleus which may optionally include a hetero atom and may optionally be fused to an aromatic nucleus.

The cycloalkan(di)one nuclei may contain a hetero atom such as, for example, N, S or O and may carry substituents such as, for example, —OH, alkyl or aryl. In formula I, ring C may be substituted with, for example, an alkyl, alkoxy or N $R_6$ $R_7$ where $R_6$ and $R_7$ have the meanings specified above. The nitrogen containing heterocyclic ring formed by $R_{15}$ and $R_{14}$ in formula I is preferably quinoline, benzoxazole, benzothiazole, benzoselenazole, naphthothiazole, naphthoselenazole or benzo-2,3-dihydroindole.

Specific examples of perester compounds in accordance with the present invention are shown in Formulae 1 to 96. Particularly preferred per esters are 2-(4'-butyl peroxy carbonylbenzoyl)methylene-3-methyl benzo thiazoline (Formula 25), 2-(4'-benzoyl-4"-t-butyl peroxy carbonyl benzoyl) methylene-3-methyl naptho-thiazoline (Formula 26), 2-(4',4"-bis-t-butyl peroxy carbonyl benzoyl) methylene-3-methyl benzoselenazoline (Formula 27), 2-(4'-t-butylperoxy carbonyl)benzylidene-indan-1-one (Formula 55), 2-(4'-t-butylperoxycarbonyl) benzylidene-5-diethylaminoindan-1-one (Formula 60), and 4-(4'-p-diethylaminobenzylidene benzoyl)-t-butylperbenzoate (Formula 94).

The perester compounds may be prepared by conversion of appropriate carboxylic acids by two general methods:

(1) Conversion of the acid to the corresponding acid chloride by reaction with thionyl chloride, followed by reaction of the isolated acid chloride with a hydroperoxide in the presence of triethyl-amine at a temperature below 5° C.

(2) Conversion of the acid to the corresponding imidazolide by reaction with 1,1'-carbonyl-diimidazolide. The imidazolide is then converted to the perester in situ by reaction with a hydroperoxide at a temperature below 5° C.

Appropriate carboxylic acid precursors may be prepared as follows:

Compounds of Formulae 1-4

Anthroquinone-2-carboxylic acids are prepared by conventional oxidation of corresponding 2-methylanthroquinone as described by Whitmore and Carnalon (Journal of the American Chemical Society 958, 51, 1929).

Compounds of Formulae 5-7

Suitable acids (fluorenone-2- and fluorenone-4-carboxylic acids) are available commercially from Aldrich or may be prepared (fluoroenone-3-carboxylic acid) by the method described in Kruber (Ber, 1382,65, 1932).

Compounds of Formulae 8-14

Suitable thioxanthone and xanthone carboxylic acid may be prepared by the methods described in GB Patent Specification No. 2 050 378.

Compounds of Formulae 15-24

Suitable precursors may be prepared by reacting carboxy aryl ketones with arylaldehydes by the methods described in U.S. Pat. Specification No. 4,162,162. The carboxy arylketones may be prepared by the methods described by Allinger and Jones (Journal of Organic Chemistry 70,27, 1962).

Compounds 25–50

These compounds may be prepared by methods illustrated by the following typical examples:

(A) Preparation of the Compound of Formulae 25

To an ice-cooled solution of terephthaloyl chloride (2.33 g) in toluene (60 ml) was added a solution of t-butylhydroperoxide (1.29 g of 80%) and triethylamine (1.22 g) in 1:1 diethylether/toluene (30 ml), dropwise over 1 hour. The temperature of the stirred solution was maintained below 5 deg. C. during the addition.

1,2-dimethylbenzothiazolium p-toluene sulphonate (3.35 g) was added to the above solution, followed by a solution of triethylamine (2.33 g) in toluene (15 ml) dropwise over a half hour at 10–15 deg. C. The reaction mixture was stirred for 2 hours at room temperature and then filtered. The filtrates were extracted with dilute hydrochloric acid (approx. 1M), washed with water and dried over anhydrous magnesium sulphate. Solid product was isolated after the removal of excess solvent from the dried extracts on a rotary evaporator. Recrystallization of this material in ethyl acetate gave (1.4 g), m.p. 160 deg. C. (decomp.).

(B) Preparation of the Compound of Formula 27

4-t-Butylperoxycarbonylbenzoyl chloride (BPCBC) was prepared as described in the first paragraph of (A). The product was isolated as a colourless oil which slowly solidified when stored in the refrigerator after solvent had been evaporated from the filtrate of the reaction mixture.

A mixture of 1,2-dimethylbenzo-selenazolium-p-tosylate (1.78 g), BPCBC (2.75 g) and dry pyridine (10 ml) was heated on a steam bath for 2 hours. The resultant mixture was diluted to a volume of 100 ml with toluene, stirred and the solution was separated from a tarry residue which had formed. The toluene solution was washed with water and then dried over magnesium sulphate.

The product was isolated after the removal of excess solvent from the dried solution on the rotary evaporator. Recrystallisation of this material in ethyl acetate gave a product having a melting point of 120° C. (decomposes).

(C) Preparation of the Compound of Formula 40

To a stirred solution of 1,3,3-trimethyl-2 methyleneindoline (3.6 ml) in dry toluene (20 ml) was added, dropwise, a solution of BPCBC (6.1 g) in dry toluene (15 ml). When the addition was complete, the mixture was heated to 60° C. and maintained at this temperature for 1½ hours before filtering. After cooling to room temperature the toluene solution was extracted with base and washed with water before drying over magnesium sulphate. A red solid was obtained from the toluene solution after removal of solvent on a rotary evaporator. Recrystallisation of this material in chloroform/methanol gave a product having a melting point of 76° C. (decomposes).

Compounds of Formulae 51-90

Suitable carboxylic acid precursors may be prepared by base catalysed condensation of arylaldehydes with cycloalkanones or aryl ketones as illustrated by the following preparations.

2-(4'-carboxyl) benzylideneindan-1-one

Indan-1-one (1.32 g) and 4-carboxylbenzaldehyde (1.50 g) were added to ethanol (15 ml). The resultant mixture was heated to reflux before adding a 10% w/v aqueous solution of sodium hydroxide (15 ml). Refluxing was continued for 1 hour. On cooling, the reaction mixture was drowned out into 1M hydrochloric acid (25 ml) to yield a white solid which was collected at the pump, washed acid free with water and dried. The yield of product was 2.54 g, m.p. 208-211 deg. C. (decomp.).

4-(4'-dimethylaminocinnamoyl) benzoic acid

4-Acetylbenzoic acid (1.5 g) and 4-dimethylaminobenzaldehyde (1.38 g) were warmed in 10% aqueous caustic soda (35 ml) until dissolved. The solution was allowed to cool, with stirring. An oil was formed which crystallised to give a red-brown solid (sodium salt) which was filtered off and converted to the acid with warm 1M acetic acid. The product was recrystallised from ethanol and had a melting point of 246°-249° C.

Compounds of Formulae 91-96

These compounds may be prepared from the triphenyl phosphonium salt of 4-(4'-bromomethyl-benzoyl) methylbenzoate, which may be prepared by the procedure described by Gupta et al. (Journal Polymer Science 855 19 1981). The procedures to convert the phosphonium salt through to the final product are illustrated by the following examples.

Preparation of the Compound of Formula 92

(i) Preparation of 4-(4'-benzylidenebenzoyl) methyl benzoate

To an ice-cooled solution of the triphenylphosphonium salt of 4-(4'-bromomethylbenzoyl) methylbenzoate (17.85 g) in methanol (100 ml) was added, dropwise, a solution of sodium methoxide (1.62 g) in methanol (40 ml), followed by benzaldehyde (3.3 g). A pink precipitate was formed. Stirring was continued for ½ hour at room temperature before the precipitate was collected and washed. Several further crops were obtained from the filtrates. The product was recrystallised from chloroform.

(ii) Preparation of 4-(4'-benzylidenebenzoyl) benzoic acid

To a dispersion of 4-(4'-benzylidenebenzoyl) methyl benzoate (4.07 g) in toluene (120 ml) was added a solution of potassium hydroxide (0.9 g) in methanol (20 ml). The resultant mixture was stirred for 72 hours at room temperature. The resulting suspension was extracted several times with water and the aqueous portions were combined, filtered and acidified with 1M $H_2SO_4$.

(iii) Conversion of the benzoic acid

To an ice cooled solution of 4-(4'benzylidene benzoyl)-benzoic acid (1.40 g) in THF was added a solution of 1,1'-carbonyldiimidazole (0.7 g) in THF (10 ml), with stirring. After 2 hours, a solution of t-butylhydroperoxide (0.5 g of 80%) in THF (10 ml) was added slowly. Stirring was continued for a further hour at 0° C. after which the solution was filtered and the solvent removed. The resulting oil was purified by column chromatography (silica) using dichloromethane as eluant. The resultant colourless oil solidified on overnight refrigeration to give a product having a melting point of 72°-76° C.

The perester compounds of the present invention are useful in the production of photopolymerisable compositions comprising the perester compound and a polymerisable compound containing ethylenic unsaturation whose polymerisation is initiated by the perester compound on exposure to radiation. Such compositions may also include an optical sensitiser and a polymeric binder and radiation sensitive plates comprising the compositions coated into a substrate and suitable for use in the production of lithographic printing plates form the subject matter of our copending patent application of even date.

The following Examples illustrate the invention.

EXAMPLE 1

A solution in ethyl methyl ketone of a photopolymerisable composition comprising:
  3 parts by weight of the dimethacrylate ester of diglycidyl ether of bisphenol A,
  1 part by weight of a vinyl acetate/crotonic acid copolymer,
  0.15 parts by weight 4-(2', 4', 6'-trimethyl benzoyl)-t-butyl perbenzoate and
  0.15 parts by weight of Ethyl Michler's Ketone, was whirler coated onto a sheet of electrochemically grained and anodised aluminium and dried to form a radiation sensitive plate. The coating weight was 1 g per sq. m.

The dried coating was overcoated with poly(vinyl alcohol) to prevent oxygen inhibition.

The radiation sensitive plate was exposed through a continuous tone Stouffer step-wedge to ultra violet light (¼ unit from a Berkey-Ascor printing down frame) and then developed with an aqueous solution containing sodium propanoate, sodium benzoate and a surfactant. The developed image of the resultant lithographic printing plate had a step-wedge of solid 3, tail 7.

When placed on a printing press, the printing plate produced many satisfactory copies.

EXAMPLE 2

Example 1 was repeated using the four alternative optical sensitisers listed below and the developed images of the resultant printing plates had the step-wedge readings shown:

| Sensitiser | Solid/Tail |
| --- | --- |
| 2-Benzoylmethylene-3-methylnaphthothiazoline | 4.9 |
| 2-Dibenzoylmethylene-3-methylbenzoselenazoline | 2.7 |

-continued

| Sensitiser | Solid/Tail |
|---|---|
| 7-Diethylamino-4-methyl-coumarin | 3 , 7 |
| 3-Carboethoxy-7-diethylamino-coumarin | 2 , 7 |

When placed on a printing press, the printing plates produced many satisfactory copies.

EXAMPLE 3

Example 1 was repeated using 4(1'methoxybenzoyl)-t-butyl perbenzoate as the initiator. Similar results were obtained except that the radiation sensitive plate was more sensitive, producing a solid 5, tail 9 step wedge on development.

EXAMPLE 4

Example 1 was repeated except that the Ethyl Michler's Ketone was replaced by 0.15 parts by weight of 2,6-bis(4'-diethylaminobenzylidene)cyclohexanone as optical sensitiser and the plate was exposed for 20 seconds to light from a xenon arc through a Wratten 45 filter which transmits light in the range 440–540 nm. The developed image had a step wedge of solid 5, tail 13. When this sensitiser was omitted from the coating, the resultant plate gave no image when exposed under similar circumstances.

EXAMPLE 5

Example 4 was repeated using t-benzoyl-t-butylperbenzoate as the initiator and the four alternative optical sensitisers listed below. The developed images had the step-wedge readings shown:

| Sensitiser | Solid/Tail |
|---|---|
| 3,3'-Diethyloxacarbocyanine iodide | 6 , 15 |
| 3,3'-Diethyl-9-methyloxacarbocyanine iodide | 3 , 10 |
| 3,3',9-Triethyloxacarbocyanine iodide | 4 , 13 |
| 3,3'-Carbonylbis(7-diethyl-amino coumarin | 4 , 12 |

EXAMPLE 6

A piece of electrochemically grained and anodised aluminium was whirler coated with a solution in ethyl methyl Ketone of a photopolymerisable composition comprising:

3 parts by weight of the dimethacrylate ester of Example 1,
0.15 parts by weight of Ethyl Michler's Ketone, and
0.15 parts by weight of the perester initiator of Example 1.

No oxygen inhibiting layer was applied. The resultant radiation sensitive plate was exposed beneath a Stouffer step-wedge on a Laserite 65R laser exposure unit (EOCOM Corporation) with an Argon ion laser emitting at 351.1 nm and 363.8 nm. The exposure energy was 2mJcm$^{-2}$. After development as in Example 1, a step-wedge reading of solid 2, tail 9 was obtained.

EXAMPLE 7

Example 1 was repeated twice using an aromatic urethane acrylate (EBECRYL 210) and a polyester acrylate (EBECRYL 810) as the polymerisable compound. (EBECRYL is a Trade Mark of ucb s.a. of Drogenbus, Belgium). Similar results were obtained.

EXAMPLE 8

To compare the properties of the compounds of formulae 1 to 96, Example 1 was repeated using radiation sensitive plates made in accordance with Example 1 but with the initiator replaced by compounds 1 to 96. The results obtained in each case are shown in the following Table which also indicates the optical sensitiser (if used) and the exposure conditions.

The optical sensitisers indicated in the table are as follows:
EMK = Ethyl Michlers Ketone
BNTZ = 2 -Benzoylmethylene-3-methylnaphthothiazoline
DOCl = 3,3'-Diethyloxacarbocyanine iodide.

The exposure conditions were:
A = ½ unit on Berkey-Ascor frame
B = 20 seconds to Xe arc through Wratten 45 filter (transmission 440–540 nm)
C = 20 seconds to Xe arc through Wratten 47 filter (transmission 400–500 mm)

All the exposures were made through a Stouffer step-wedge. The absorbance given is the wavelength of the longest radiation having an absorbance peak.

TABLE

| Initiator Formula | Optical Sensitiser | Exposure | Step Wedge Solid Tail | Absorbance (nm) |
|---|---|---|---|---|
| 1 | EMH | A | 3 , 9 | 324 |
| 2 | " | " | 3 , 9 | 323 |
| 3 | " | " | 2 , 8 | 328 |
| 3 | DOC 1 | B | 3 , 9 | |
| 4 | "B | 1 , 7 | 396 | |
| 5 | EMH | A | 4 , 9 | 352 |
| 6 | " | " | 0 , 5 | 343 |
| 7 | " | " | 0 , 4 | 345 |
| 8 | " | " | 3 , 8 | 350 |
| 9 | NONE | " | 4 , 10 | 396 |
| 10 | " | " | 5 , 12 | 404 |
| 11 | " | " | 6 , 12 | 418 |
| 12 | " | " | 8 , 13 | 400 |
| 13 | " | " | 0 , 7 | 388 |
| 14 | " | " | 1 , 8 | 406 |
| 15 | " | C | 6 , 12 | 441 |
| 16 | " | " | 7 , 13 | 432 |
| 17 | " | " | 7 , 12 | 465 |
| 18 | " | " | 2 , 7 | 486 |
| 19 | " | " | 8 , 13 | 451 |
| 20 | " | " | 9 , 14 | 462 |
| 21 | " | " | 4 , 10 | 439 |
| 22 | " | " | 2 , 7 | 422 |
| 23 | " | " | 3 , 7 | 440 |
| 24 | " | " | 7 , 12 | 433 |
| 25 | " | A | 10 , 14 | 397 |
| 26 | " | " | 4 , 9 | 396 |
| 27 | " | " | 2 , 5 | 394 |
| 28 | " | " | 12 , 18 | 401 |
| 29 | " | A(5 units) | 2 , 5 | 373 |
| 30 | " | A | 9 , 13 | 395 |
| 31 | " | " | 3 , 8 | 392 |
| 32 | NONE | A | 8 , 13 | 404 |
| 33 | " | A | 4 , 9 | 378 |
| 34 | " | " | 5 , 11 | 385 |
| 35 | " | " | 3 , 7 | 382 |
| 36 | " | " | 9 , 13 | 397 |
| 37 | " | " | 11 , 16 | 398 |
| 38 | " | " | 8 , 14 | 406 |
| 39 | " | " | 3 , 9 | 380 |
| 40 | " | " | 10 , 14 | 395 |
| 41 | " | " | 11 , 15 | 395 |
| 42 | " | " | 2 , 8 | 417 |
| 43 | " | " | 3 , 7 | 398 |
| 44 | " | " | 3 , 7 | 397 |
| 45 | " | " | 9 , 14 | 409 |
| 46 | " | " | 7 , 13 | 407 |
| 47 | " | " | 2 , 7 | 398 |
| 48 | " | " | 2 , 6 | 372 |
| 49 | " | " | 5 , 11 | 395 |

TABLE-continued

| Initiator Formula | Optical Sensitiser | Exposure | Step Wedge Solid Tail | Absorbance (nm) |
|---|---|---|---|---|
| 50 | " | " | 0 , 5 | 404 |
| 51 | BNTZ | " | 5 , 11 | 304 |
| 52 | " | " | 1 , 8 | 312 |
| 53 | " | " | 0 , 5 | 300 |
| 54 | " | " | 2 , 7 | 340 |
| 55 | " | " | 2 , 8 | 298 |
| 56 | " | " | 3 , 9 | 301 |
| 57 | " | " | 1 , 7 | 296 |
| 58 | " | " | 2 , 9 | 311 |
| 59 | " | " | 4 , 11 | 299 |
| 60 | " | " | 6 , 12 | 378 |
| 60 | NONE | " | 3 , 9 | 378 |
| 62 | BNTZ | " | 4 , 11 | 311 |
| 62 | " | " | 1 , 6 | 315 |
| 63 | BNTZ | A | 1 , 7 | 323 |
| 64 | " | " | 1 , 7 | 303 |
| 65 | " | " | 4 , 11 | 321 |
| 66 | " | " | 3 , 8 | 304 |
| 67 | " | " | 1 , 6 | 301 |
| 68 | " | " | 3 , 8 | 308 |
| 69 | " | " | 5 , 10 | 314 |
| 70 | " | " | 2 , 7 | 288 |
| 71 | " | " | 2 , 8 | 298 |
| 72 | " | " | 4 , 11 | 312 |
| 73 | " | " | 1 , 7 | 341 |
| 74 | " | " | 2 , 8 | 306 |
| 75 | " | " | 2 , 8 | 311 |
| 76 | " | " | 4 , 11 | 313 |
| 77 | " | " | 0 , 6 | 322 |
| 78 | " | " | 0 , 5 | 311 |
| 79 | NONE | B | 2 , 7 | 443 |
| 80 | NONE | A | 3 , 8 | 406 |
| 81 | " | | 3 , 9 | 364 |
| 81 | EMK | | 6 , 11 | 364 |
| 82 | " | " | 3 , 9 | 308 |
| 83 | " | " | 1 , 7 | 300 |
| 84 | NONE | " | 2 , 8 | 402 |
| 85 | " | " | 4 , 11 | 400 |
| 86 | " | B | 2 , 9 | 425 |
| 87 | " | " | 5 , 12 | 448 |
| 88 | " | " | 3 , 10 | 477 |
| 89 | EMK | A | 4 , 10 | 328 |
| 90 | NONE | " | 3 , 9 | 386 |
| 91 | EMK | " | 6 , 12 | 308 |
| 92 | " | " | 5 , 9 | 312 |
| 93 | " | " | 3 , 8 | 341 |
| 94 | NONE | A | 5 , 10 | 400 |
| 94 | " | B | 7 , 12 | 400 |
| 95 | " | A | 6 , 11 | 412 |
| 95 | " | B | 9 , 14 | 412 |
| 96 | " | A | 4 , 10 | 428 |
| 96 | " | B | 8 , 13 | 428 |

EXAMPLE 9

Example 1 was repeated except that the amount of the initiator was increased to 0.3 parts by weight. The developed image had a step wedge of solid 12, tail 16.

EXAMPLE 10

A solution in ethyl methyl ketone of a photopolymerisable composition comprising:

3 parts by weight of the dimethacrylate ester of diglycidyl ether of bisphenol A, 1 part by weight of a vinyl acetate/crotonic acid copolymer, and 0.15 pts by weight of the photo initiator of formula (25) was whirler coated onto a sheet of grained and anodised aluminium and dried to form a radiation sensitive plate. The coating weight was 1 g.m.$^{-2}$.

The dried coating was overcoated with poly(vinyl alcohol) to prevent oxygen inhibition.

The radiation sensitive plate was exposed through a continuous tone Stouffer step-wedge to ultra violet light (0.03 unit) from a Berkey-Ascor printing down frame and developed with an aqueous solution containing sodium propanoate, sodium benzoate and a surfactant. The developed image of the resultant lithographic printing plate had a step-wedge of solid 10 tail 14.

EXAMPLE 11

Example 10 was repeated except that the solution also contained 0.15 parts by weight of Ethyl Michler's ketone as optical sensitiser. The developed image had a step-wedge of solid 11 tail 18.

EXAMPLE 12

Examples 10 and 11 were repeated using the photo initiator of formula 26.

Similar results to those of Examples 10 and 11 were obtained.

EXAMPLE 13

A piece of grained and anodised aluminium was whirler coated to a weight of 1 g.m.$^{-2}$ with a solution in ethyl methyl ketone of a photopolymerisable composition comprising 3 parts by weight of the monomer of Example 10, 1 part by weight of phthaloylated poly(vinyl butyral), and 0.15 parts by weight of the initiator of formula 94.

The resultant radiation sensitive plate was exposed through a Stouffer step-wedge for 20 seconds to light from a xenon arc through a Wratter 45 filter which transmits light in the range 440-540 nm. The developed image of the resultant lithographic printing plate had a step-wedge of solid 9, tail 14.

EXAMPLE 14

Example 13 was repeated except that the radiation sensitive plate was exposed using a Laserite 65R laser exposure unit (EOCOM Corporation) with an Argon ion laser emitting at 488 nm. The exposure energy was 5 mJcm$^{-2}$. After development a step-wedge reading of solid 3, tail 8 was obtained.

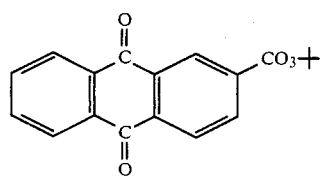

(1)

-continued
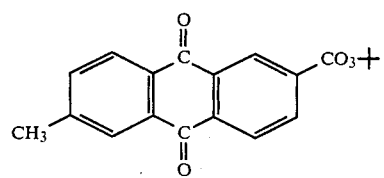 (2)
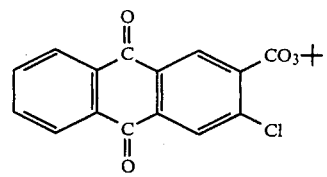 (3)
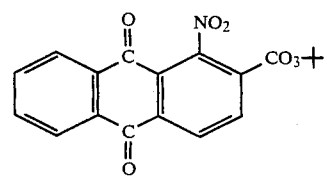 (4)
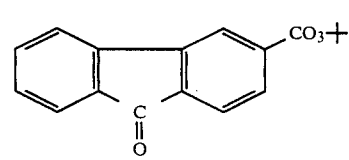 (5)
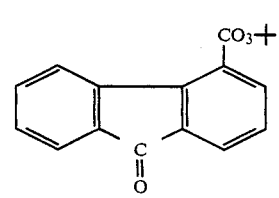 (6)
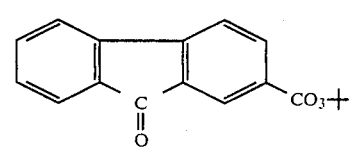 (7)
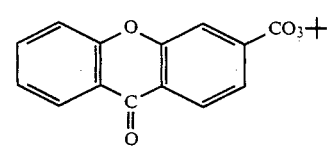 (8)
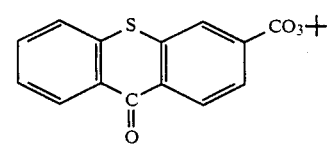 (9)
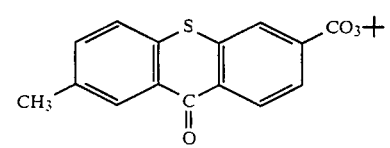 (10)

-continued
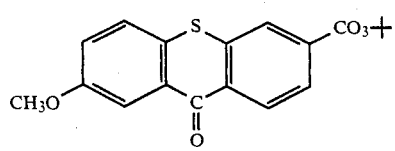 (11)
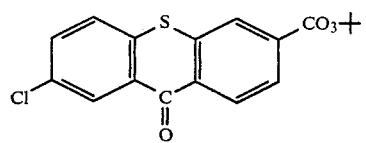 (12)
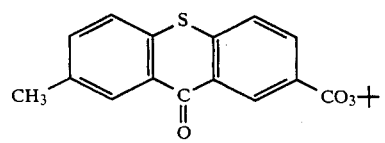 (13)
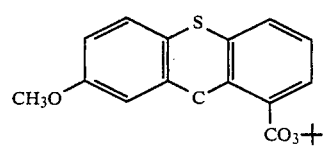 (14)
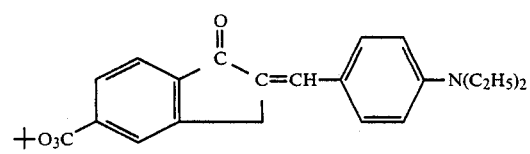 (15)
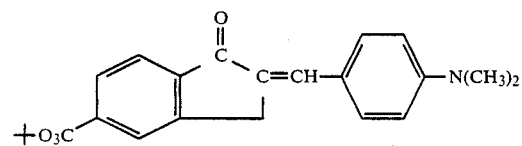 (16)
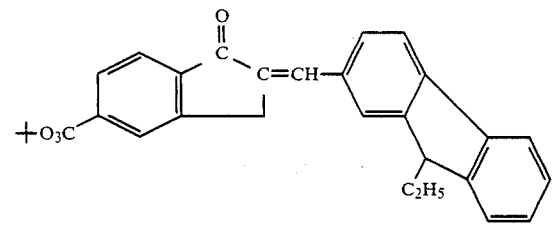 (17)
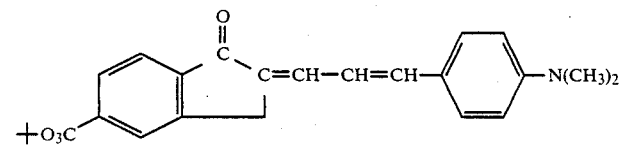 (18)
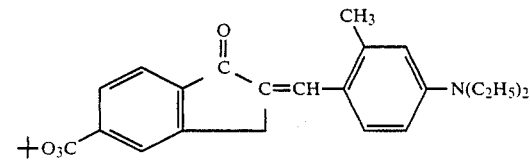 (19)

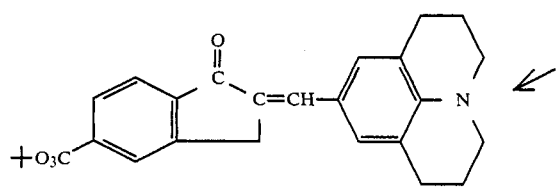
(20)
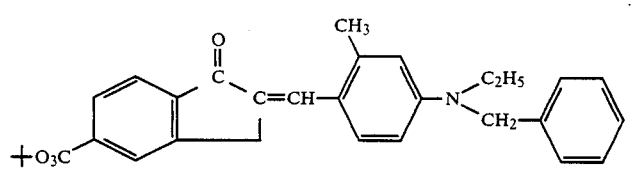
(21)
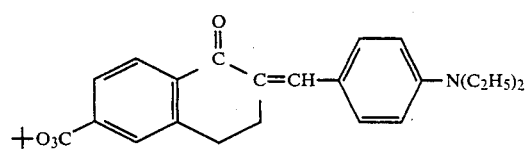
(22)
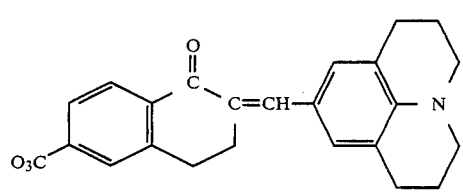
(23)
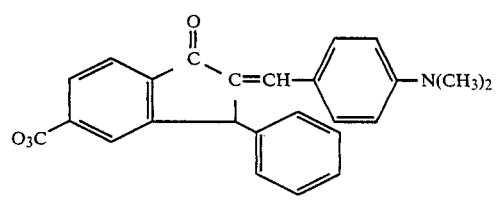
(24)
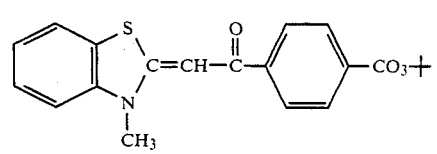
(25)
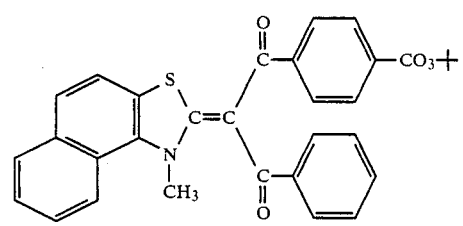
(26)
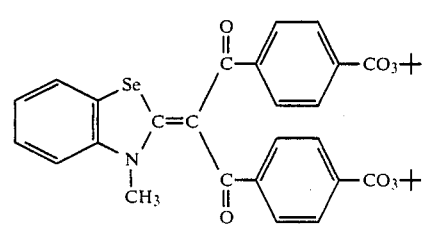
(27)

-continued
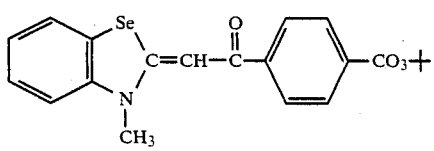 (28)
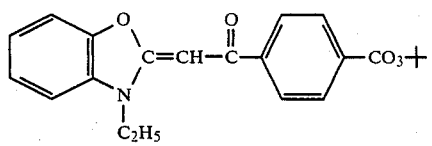 (29)
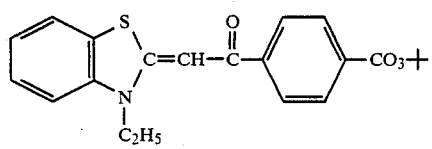 (30)
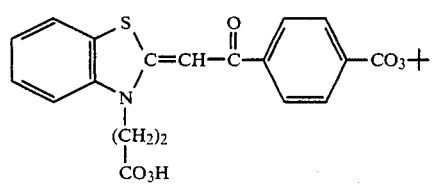 (31)
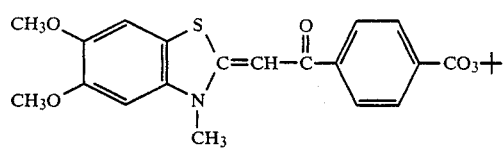 (32)
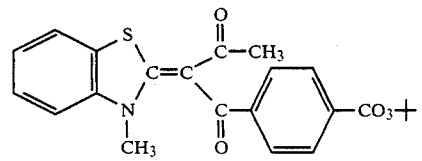 (33)
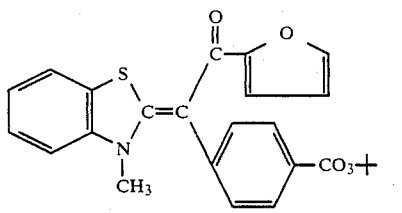 (34)
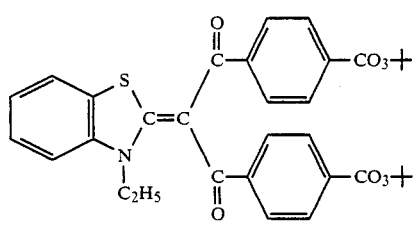 (35)
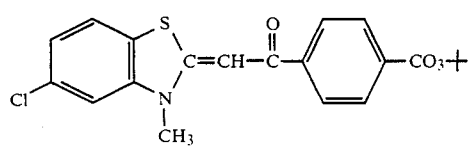 (36)

-continued
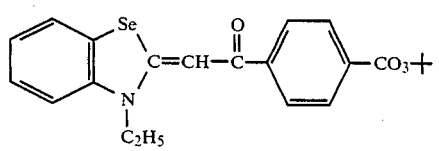 (37)
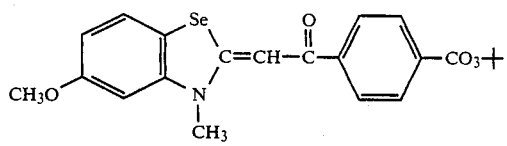 (38)
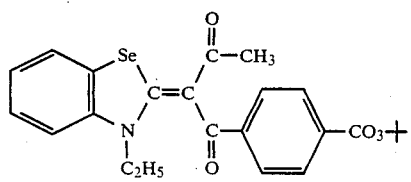 (39)
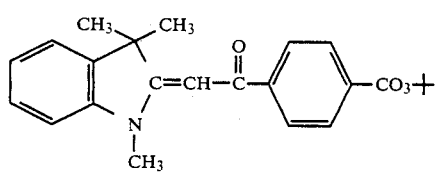 (40)
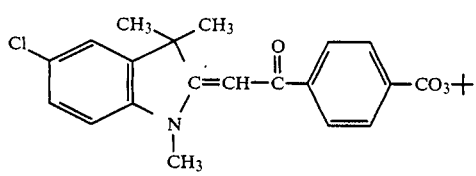 (41)
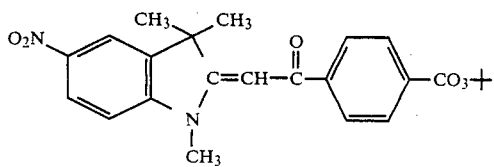 (42)
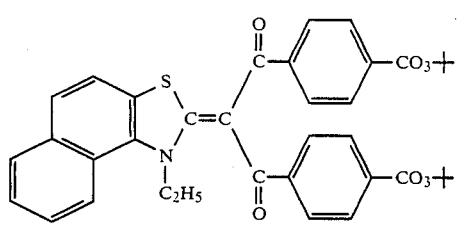 (43)
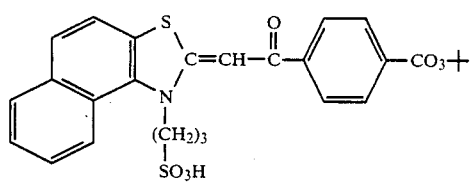 (44)
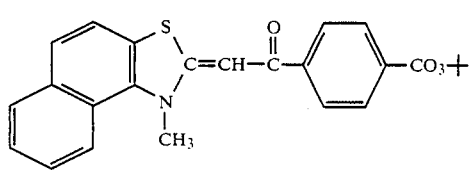 (45)

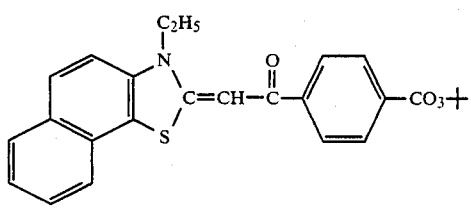
(46)
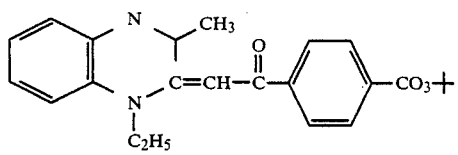
(47)
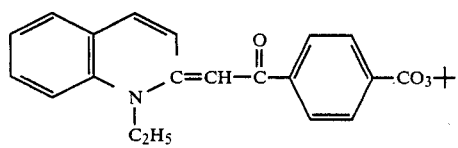
(48)
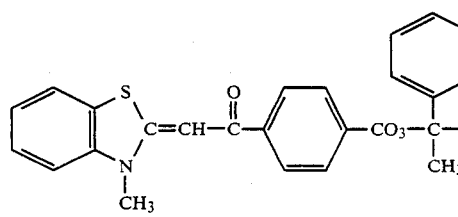
(49)
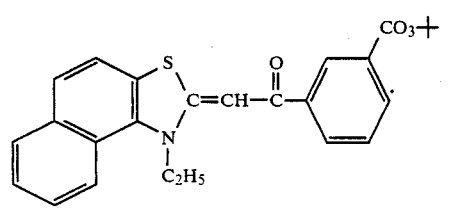
(50)
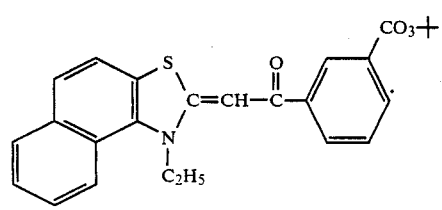
(51)
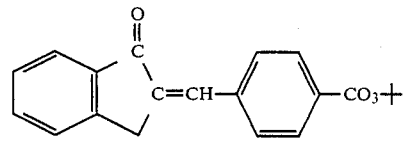
(52)
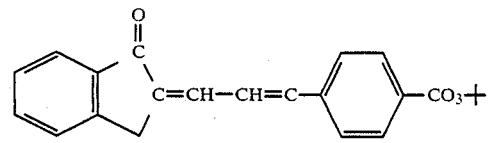
(53)
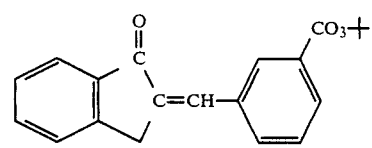
(54)
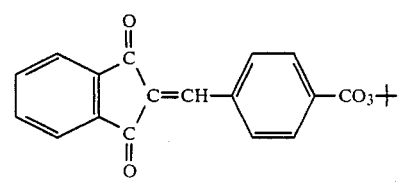

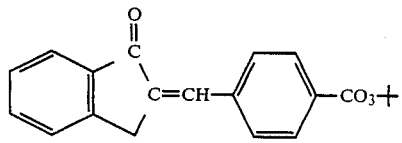
(55)
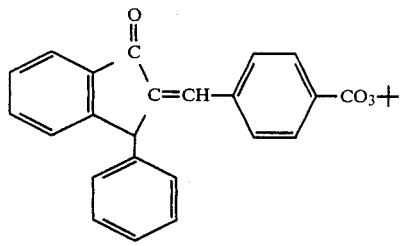
(56)
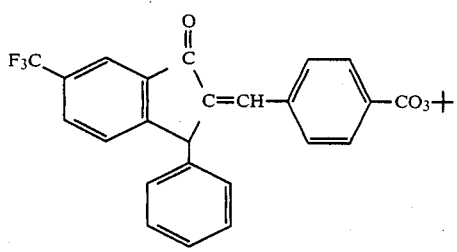
(57)
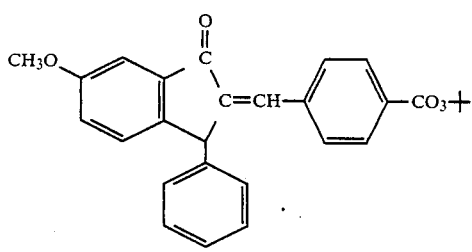
(58)
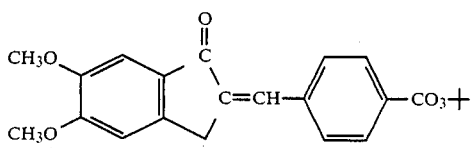
(59)
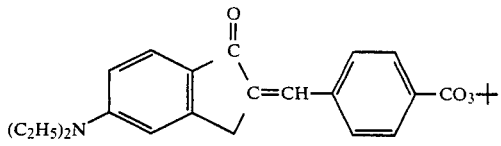
(60)
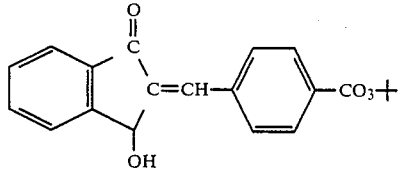
(61)
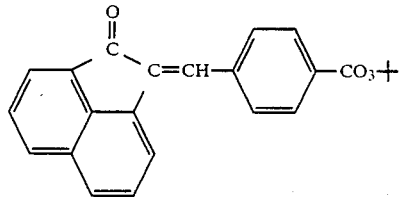
(62)

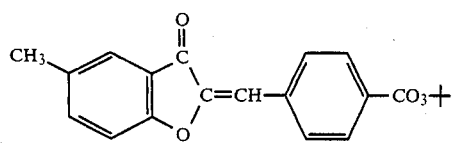
(63)
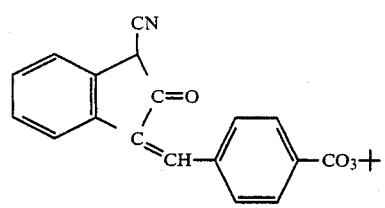
(64)
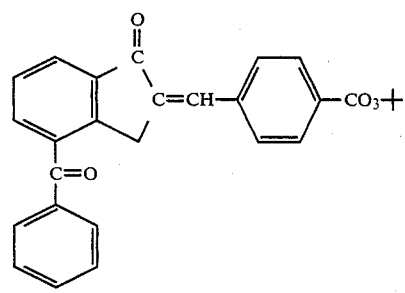
(65)
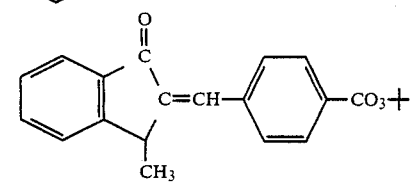
(66)
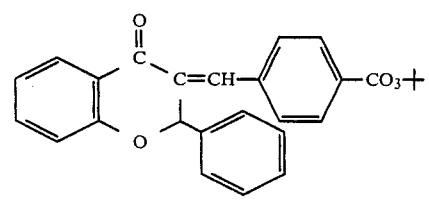
(67)
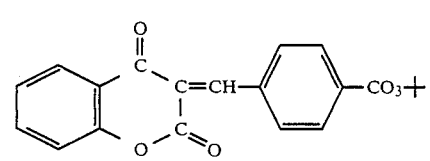
(68)
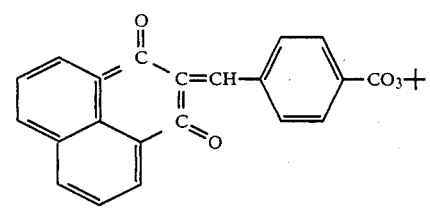
(69)
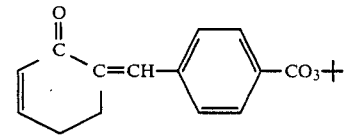
(70)
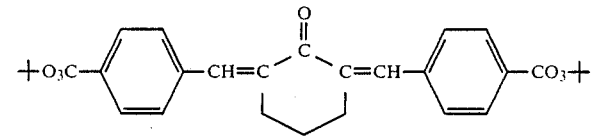
(71)

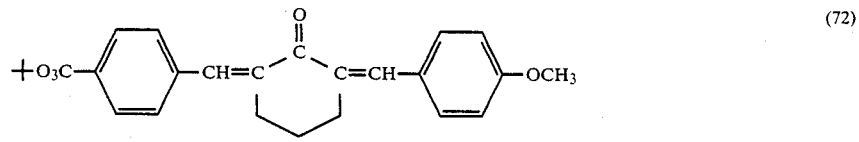
(72)
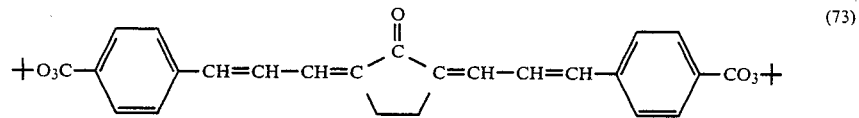
(73)
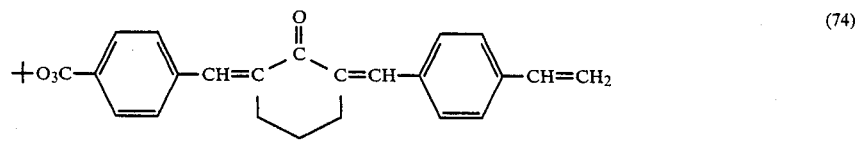
(74)
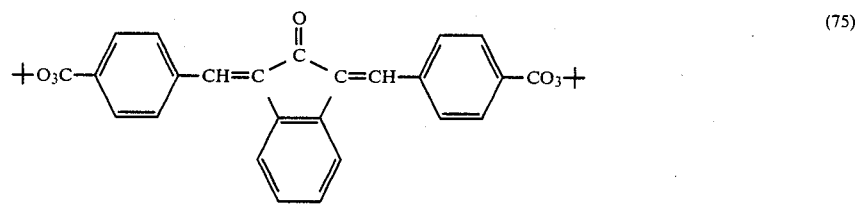
(75)
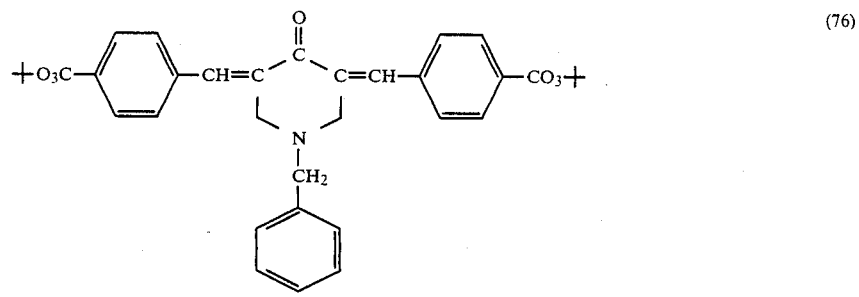
(76)
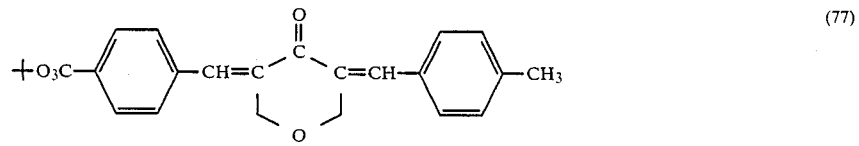
(77)
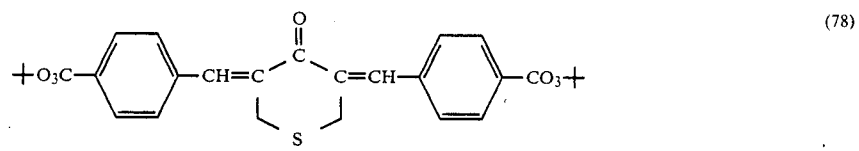
(78)
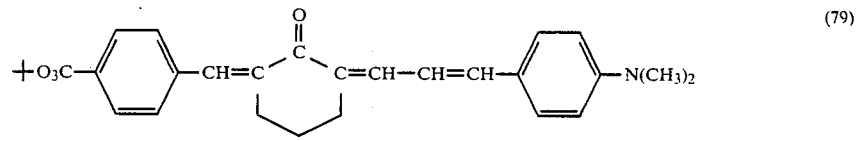
(79)
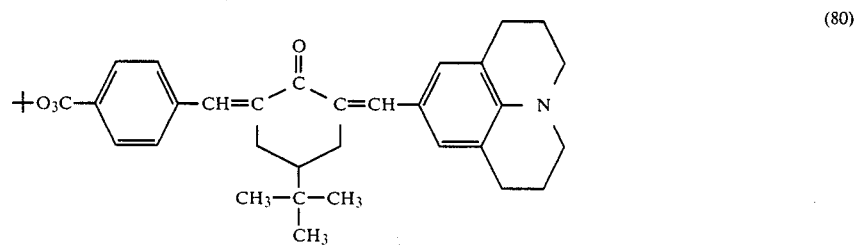
(80)

-continued
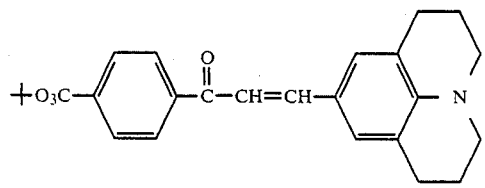 (87)
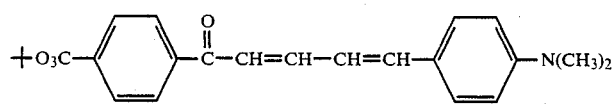 (88)
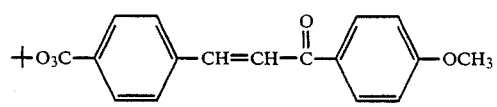 (89)
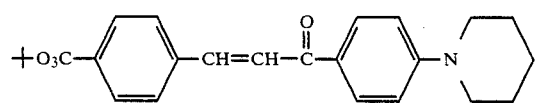 (90)
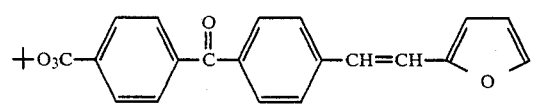 (91)
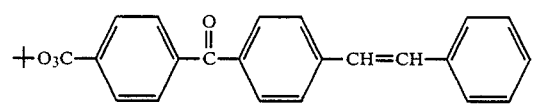 (92)
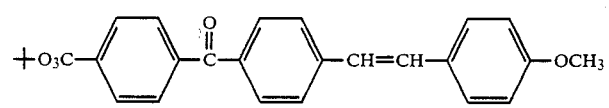 (93)
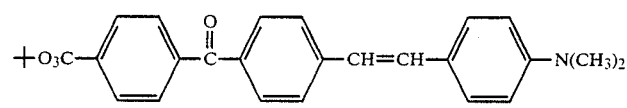 (94)
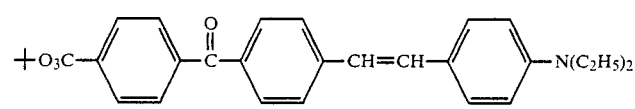 (95)
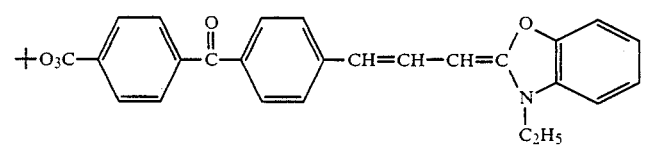 (96)
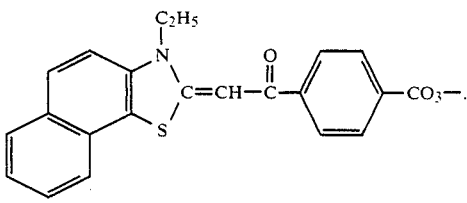
We claim:
1. A perester compound having the general formula:
* * * * *

UNITED STATES PATENT AND TRADEMARK OFFICE
CERTIFICATE OF CORRECTION

PATENT NO. : 4,946,960
DATED : August 7, 1990
INVENTOR(S) : Wade, et al.

It is certified that error appears in the above-identified patent and that said Letters Patent is hereby corrected as shown below:

Column 2, line 36, change "an cycloalkan" to --a cycloalkan--.

Column 3, line 11, change "m, n, t u and p" to --m, n, t, u and p--.

Column 3, lines 16-17, change " members optionally cycloalkan" to --members necessary to complete a cycloalkan--.

Column 3, line 32, after "4'" insert -- -t- --.

Column 7, line 41, after "amino" insert --)--.

Column 8, in the Table, for Initiator 4, shift the data "B   1,7   396" one column to the right.

Column 15, formula 20, delete "←".

UNITED STATES PATENT AND TRADEMARK OFFICE
CERTIFICATE OF CORRECTION

PATENT NO. : 4,946,960

DATED : August 7, 1990

INVENTOR(S) : Wade, et al.

It is certified that error appears in the above-identified patent and that said Letters Patent is hereby corrected as shown below:

Column 17, formula 31, change

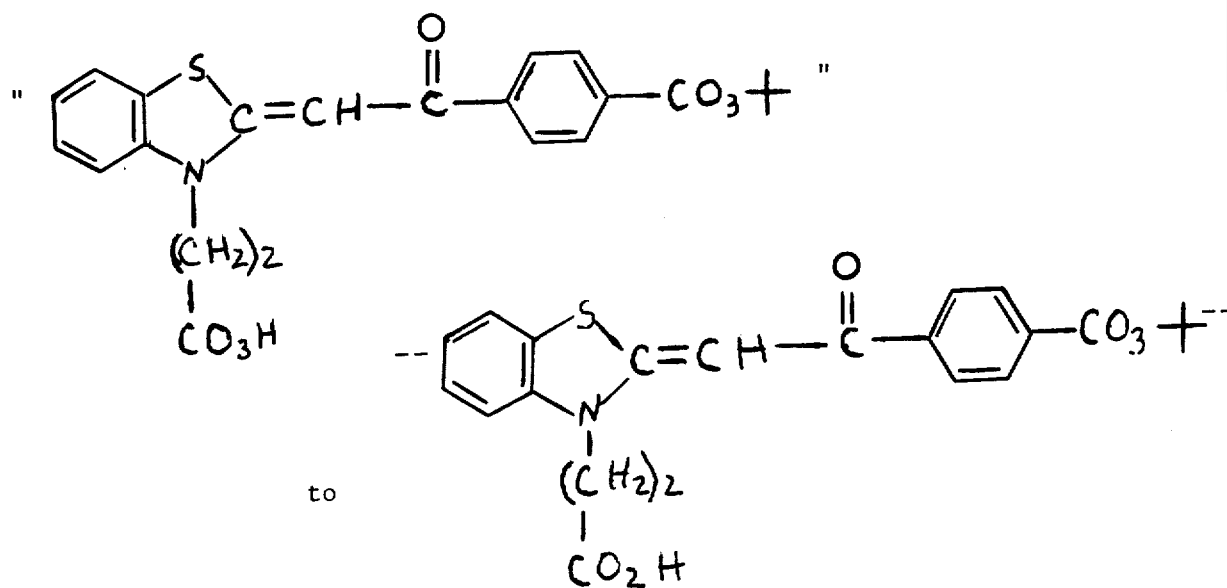

Signed and Sealed this

Eighth Day of December, 1992

Attest:

DOUGLAS B. COMER

Attesting Officer

Acting Commissioner of Patents and Trademarks